US005225581A

United States Patent [19]

Pintauro

[11] Patent Number: 5,225,581

[45] Date of Patent: Jul. 6, 1993

[54] ELECTROCATALYTIC PROCESS FOR THE HYDROGENATION OF EDIBLE AND NON-EDIBLE OILS AND FATTY ACIDS

[75] Inventor: Peter N. Pintauro, Kenner, La.

[73] Assignee: Tulane Educational Fund, New Orleans, La.

[21] Appl. No.: 538,157

[22] Filed: Jun. 14, 1990

[51] Int. Cl.[5] .............................................. C07C 51/36

[52] U.S. Cl. .................................... 554/147; 554/141; 204/50 R; 204/73 R; 204/76

[58] Field of Search ................ 260/409; 554/141, 147; 204/59, 73, 76

[56] References Cited

U.S. PATENT DOCUMENTS 2,147,177 2/1939 Seto et al. ............................ 204/31
3,925,172 12/1975 Voorhies ............................... 204/72
4,120,763 10/1978 Breda et al. .......................... 204/73
4,161,483 7/1979 Cahen .................................. 260/409
4,163,750 8/1979 Bird et al. ........................... 260/409
4,228,088 10/1980 Kuiper ................................ 260/409
4,229,361 10/1980 Cahen ................................. 260/409
4,278,609 7/1981 Kuiper ................................ 260/409
4,307,026 12/1981 Kuiper ................................ 260/409
4,326,932 4/1982 Froling et al. .................... 204/59 R
4,399,007 8/1988 Froling et al. ........................ 204/59

OTHER PUBLICATIONS

"Trimming the fat from hydrogenation", High Technology, p. 9, 1987.
"From the AIChE: electrocatalytic hydrogenation . . . ", Chemical Week p. 21., Nov. 12, 1986.
"Hydrogentation Innovation", Oils and Fats International, Issue Two, p. 6, 1987.
K. Park et al., "Flow Reactor Studies of the Paired Electro–Oxidation and Electroreduction of Glucose", J. Electrochem. Soc., 132, pp. 1850–1855 (1985).
K. Park et al., "Current efficiencies and regeneration of poisoned, Raney nickel in the electrohydrogenation of glucose to sorbitol", J. Appl. Electrochem. 16, pp. 941–946 (1986).
P. N. Pintauro, et al., "The Electrochemical Hydrogenation of Organic Compounds on Raney–Type Metal Catalysts", Electrochemical Engineering Applications, vol. 83, No. 254, pp. 34–39 (AIChE Symposium Nov. 2–7 1986).
L. M. V. Tillekeratne et al., "Electrochemical Reduction of Rubber Seed Oil to Stearic Acid", J. Applied Electrochemistry 11, pp. 281–285 (1981).
Y. Song et al., "The Electrochemical Synthesis of Aminonitriles" I. H–Cell Studies with Adiponitrile and Azelanitrile, Journal of Applied Electrochemistry (in press, submitted Mar. 1989).
J. D. Ray et al., "Empirical Modeling of Soybean Oil Hydrogenation" JAOCS 62, No. 8, pp. 1218–1222 (1985).

(List continued on next page.)

*Primary Examiner*—Jose G. Dees
*Assistant Examiner*—D. D. Carr
*Attorney, Agent, or Firm*—Morgan & Finnegan

[57] ABSTRACT

An electrocatalytic process for hydrogenating an unsaturated fatty acid, triglyceride, or mixtures thereof as an oil or fat is described. Current is passed through a cathode and hydrogen is generated in situ on the high surface area, low hydrogen overvoltage catalytic material used as the cathode in a reactor containing a liquid reaction medium (electrolyte) comprised of oil and/or fat, water and/or an organic solvent (e.g. t-butanol), and a supporting electrolyte salt. Typical catalytic cathodes comprise a granular or powdered Raney metal or an alloy thereof, platinum black, ruthenium black, or finely divided carbon powder containing platinum, palladium, or ruthenium. Typical supporting electrolyte salts include sodium p-toluenesulfonate, tetraethylammonium p-toluenesulfonate, and sodium or potassium phosphate monobasic.

A novel partially hydrogenated oil or fat product is obtained when the above process is carred out at temperatures less than 75° C. The product is characterized by a trans isomer content lower than that of a hydrogenated product which is prepared by a high temperature, chemical catalytic process. The specific isomer selectivity index of cis to trans isomer was 0.36 or less.

27 Claims, 1 Drawing Sheet

OTHER PUBLICATIONS

S. Koritala, "Homogeneous Catalytic Hydrogenation of Soybean Oil: Palladium Acetylacetonate" JAOCS 62, No. 3, pp. 517-520 (1985).

T. Chiba et al., "Electrocatalytic Reduction Using Raney Nickel", Bull. Chem. Soc., Jpn. 56, pp. 719-723 (1983).

L. L. Miller et al., "Electrocatalytic Hydrogenation of Aromatic Compounds" J. Org. Chem. 43, No. 10, pp. 2059-2061 (1978).

"The Electrocatalytic Hydrogenation of Organic Compounds at Raney-Type Catalytic Cathodes", Peter N. Pintauro, proposal submitted in Oct. 1986 to American Chemical Society.

Effect of Dietary Trans Fatty Acids on High-Density and Low-Density Lipoprotein Cholesterol Levels in Healthy Subjects, by R. P. Mensink et al. in N. Engl. J. Med. 323, pp. 439-445 (1990).

ELECTROCATALYTIC PROCESS FOR THE HYDROGENATION OF EDIBLE AND NON-EDIBLE OILS AND FATTY ACIDS

BACKGROUND OF THE INVENTION

The hydrogenation of oils or fats is carried out to produce a more oxidatively stable product and/or to change a normally liquid oil into a semi-solid or solid fat with characteristics designed for a particular product application. The goal of an oil hydrogenation processing scheme is to reduce the number of unsaturated fatty acids or fatty acid constituents present in the triglycerides.

The majority of commercially hydrogenated oils and fats are processed with batch reactor equipment using high temperatures, chemical catalysts, and hydrogen gas supplied to the reactor at elevated pressures. The hydrogenation catalysts used include Raney and supported nickel catalysts, promoted nickel catalysts containing palladium, copper, or zirconium, and copper chromite catalysts. The rate of hydrogenation is dependent on the reaction temperature, the nature of the oil or fat, the activity and concentration of the catalyst, and the rate at which hydrogen gas and unsaturated oil or fat are supplied to the hydrogenation reactor. Typical reaction pressures and temperatures are in the range of 10–60 psig and 150°–225° C., respectively. These elevated temperatures and pressures are required to solubilize sufficiently high concentrations of hydrogen gas in the oil/catalyst or fat/catalyst reaction medium so that the hydrogenation reaction proceeds at acceptably high rates. Unfortunately, high reaction temperatures promote a number of deleterious side-reactions such as the production of trans fatty acid isomers, the oxidation of double bonds leading to flavor reversion and rancidity, and the formation of cyclic aromatic fatty acids.

In traditional high temperature hydrogenations some of the unsaturated cis isomers of fatty acids or triglycerides are converted to the trans isomers. This transformation may cause the hydrogenated oil or fat to have undesirable properties and may affect the nutritional value of the oil or fat.

For example, as discussed by J. D. Ray et al. in "Empirical Modeling of Soybean Oil Hydrogenation", J. Am. Oil. Chem. Soc., 62, 1222 (1985), the total percent of trans isomers in a partially hydrogenated soybean oil product ranges from 40.8% to 60.8%, whereas the initial oil contains only 3.5% trans isomers. In this study, the temperature was between 138° C. and 204° C., the pressure was between 5 and 50 psig, and the catalyst was nickel. A common measure of quantifying the extent of cis to trans isomer conversion during the hydrogenation of an oil or fat is the specific isomer selectivity index, defined as the percent of trans isomers in the hydrogenated oil product divided by the change in Iodine Value between the starting oil and hydrogenated product. A typical commercial hydrogenated corn oil margarine, for example, has an Iodine Value of approximately 93, whereas the unreacted liquid corn oil starting material has an Iodine value of approximately 128. The total trans isomer content of the hydrogenated corn oil margarine is 20.5%, thus the specific isomer selectivity index is 0.590, i.e., 20.5/(128-93). Hydrogenated oil products from typical high temperature (60°–170° C. ) hydrogenation processes have a specific isomer selectivity index in the range of 0.36 to 1.79, indicating high trans isomer concentrations [see, for example, "Homogeneous Catalytic Hydrogenation of Soybean Oil: Palladium Acetylacetonate", J. Am. Oil. Chem., 62, 517 (1985)].

Although electrochemical reductions of simple unsaturated organic compounds have been widely studied over the past fifty years, very little work has been carried out on the electrochemical reduction of oils or fats. An electrochemical technique for adding hydrogen to an oil is described by L. M. V. Tillekeratne, et al. in "Electrochemical Reduction of Rubber Seed Oil to Stearic Acid", J. Applied Electrochemistry 11, pp. 281-285 (1981). This electrochemical reduction of rubber seed oil via a direct electron transfer mechanism was studied using cathodes such as graphite, copper, stainless steel, lead, nickel, palladium-plated graphite, and Monel (65% nickel and 35% copper). The optimum cathode material was found to be Monel, which is a high hydrogen overvoltage material. No reduction was observed on low hydrogen overvoltage materials such as platinum and nickel.

Electrocatalytic hydrogenations using Raney nickel or similar low hydrogen overvoltage catalysts as cathode materials have been reported by a number of investigators [T. Chiba et al., Bull. Chem. Soc. Jpn., 56 (1983) 719; L. L. Miller et al., J. Org. Chem., 43 (1978) 2059; I. V. Kirilyus et al., Sov. Electrochem., 15 (1979) 1330; K. Park et al., J. Electrochem. Soc., 132, (1985) 1850]. These studies have dealt with the electrochemical hydrogenation of unsaturated hydrocarbons, phenols, ketones, nitro-compounds, and sugars rather than unsaturated fatty acids.

There is a need for a more efficient and alternative method of hydrogenating unsaturated fatty acids and the unsaturated fatty acid constituents in the triglycerides found in oils and fats.

SUMMARY OF THE INVENTION

The present invention is directed to an electrocatalytic process for partially or completely hydrogenating a single unsaturated fatty acid or mixtures of one or more fatty acids having different degrees of unsaturation. Most single or multiple double bond fatty acids will have the general formula $CH_3—(CH_2)_n—[CH{=}CH—(CH_2)]_m—(CH_2)_x—COOH$, where n, m, and x are at least 1 and m is greater than 1 when the fatty acid is a multiple double bond fatty acid. The process is applicable to unsaturated fatty acids and/or triglycerides and is especially useful for edible oils or fats because of the low temperatures that can be used.

As used herein, the term electrocatalytic hydrogenation (reduction) refers to a hydrogenation carried out using a high surface area conductive catalyst as the cathode, whereas the term electrochemical hydrogenation (reduction) refers to a hydrogenation carried out using a low surface area conductive material with little or no catalytic properties.

The electrocatalytic hydrogenation reaction can be carried out in either a batch or continuous flow reactor using less complex and less expensive reactors than other hydrogenation processes.

The cathode used in the reaction is a high surface area, low hydrogen overvoltage catalytic metal (e.g., Raney nickel), a catalytic alloy (e.g., Raney nickel-molybdenum), or a conducting solid containing a precious metal catalyst (e.g., palladium-coated graphite powder). Hydrogen is generated on the catalyst surface by the electrochemical reduction of protons or water in an adjacent liquid medium (the electrolyte). The hydrogen generated reacts with the unsaturated fatty acids to produce the saturated (hydrogenated) or partially saturated (hydrogenated) product. Since hydrogen is generated in situ directly on the catalyst surface by passing current through the conducting catalytic cathode, high operating temperatures and pressures are not required.

The reaction can be carried out at low temperatures, preferably in the range of about 15°-75° C., most preferably about 25°-60° C., which is significantly lower than the temperatures used in commercial catalytic hydrogenation reaction schemes, which are typically 150°-225° C. By maintaining a low reaction temperature, it is possible to minimize unwanted isomerization reactions, thermal degradation of the oil, and deleterious oxidation reactions. However, there is no upper temperature limitation for the electrocatalytic hydrogenation reactions and, if desired, such reactions can be carried out at temperatures above 75° C. By maintaining a high applied current, a satisfactory hydrogenation rate can be attained even at low or moderate temperatures.

Water and/or a suitable proton-containing organic solvent medium is used as the electrolyte. The reaction medium may be a single phase or two phases (oil and solvent). The water and/or solvent are used in the proportions needed to produce the desired phase. When the medium is either water, an organic solvent, or mixtures thereof, a supporting electrolyte salt must be added to increase the electrical conductivity of the solution. Suitable solvents and salts are discussed hereafter.

Advantages of the electrocatalytic hydrogenation process are: (1) hydrogen and catalyst may be used more efficiently, thus requiring lower catalyst loading of the reactor; (2) there is little free hydrogen gas present, thus reducing the risk of explosion and fire; (3) the concentration of hydrogen on the catalyst metal surface can be easily controlled by adjusting the applied current (or applied electric potential), which may lead to improved product selectivity; (4) the operating temperatures are low, thus minimizing thermal degradation of the reactants and products and/or unwanted homogeneous side reactions; and (5) corrosion of the metal catalyst is less, thus reducing or eliminating the concentration of metal ion contaminants in the hydrogenated product.

The present invention is also directed to a novel partially hydrogenated product selected from the group consisting of a partially hydrogenated fatty acid, a partially hydrogenated triglyceride, or mixtures thereof as an oil or fat, wherein the partially hydrogenated product is characterized by a trans isomer content lower than that of a partially hydrogenated product which is prepared by a high temperature process. The novel partially hydrogenated product is prepared by the present electrocatalytic process at a temperature of less than about 75° C. The product is unique in that it has a specific isomer selectivity index less than 0.36, preferably less than or equal to 0.31, and as low as or lower than 0.166.

The preferred catalytic cathode for use in the preparation of the novel hydrogenated product is a Raney nickel powder or polytetrafluoroethylene bonded Raney nickel sheet. Higher cis to trans ratios should be achieved with other high surface area, low hydrogen overvoltage catalytic cathodes. The preferred temperature for use in the preparation of the novel hydrogenated product is 50° C. or less and, if a higher cis to trans isomer ratio is desired, the most preferred temperature is 25° C. or less.

DETAILED DESCRIPTION OF THE PREFERRED EMBODIMENTS

The reaction of interest in this process is the addition of hydrogen to the double bond moieties of fatty acids or the fatty acids present in the triglycerides. The source of hydrogen is the water, organic solvent, or mixtures thereof. The overall reaction can be written as follows:

$$R_m + nH^+ + ne^- \rightarrow R_mH_n,$$

where $R_m$ denotes an unsaturated fatty acid with a total of m double bonds. For complete saturation of all double bonds present in the fatty acids $n=2m$ and for partial saturation $n=2q$, where $1<q<m$.

In this electrocatalytic hydrogenation, hydrogen atoms are generated on the high surface area, low hydrogen overvoltage catalyst by passing electric current through the catalyst material. It is necessary to insure that the fatty acid or triglyceride contacts the catalyst surface. If contact is not made, electro-generated hydrogen atoms will combine on the catalyst surface and produce molecular hydrogen ($H_2$) which will not then react with the fatty acid or triglyceride. In this situation $H_2$ will bubble-off the catalyst surface as $H_2$ gas.

Two techniques which insure intimate contact of the fatty acid or triglyceride with the catalyst surface are: (1) complete solubilization of the fatty acid and/or triglyceride in a suitable organic or organic/aqueous solvent and (2) thorough dispersion of the fatty acid and/or triglyceride in water, a suitable organic solvent, or mixtures thereof. In some cases to stabilize the dispersion it may be advisable to use an emulsifier as the supporting electrolyte or add an emulsifying agent to the solvent/supporting electrolyte/fatty acid and/or triglyceride reaction medium.

Suitable oils for use herein include edible oils derived from a vegetable, grain, nut, or fish, as well as non-edible oils. Suitable fats include edible fats such as an animal fat, as well as non-edible fats. Typical edible oils include soybean, sunflower, safflower, cottonseed, corn, canola (rape seed), coconut, rice, peanut, palm, and olive oils. The primary fatty acid constituents of these oils which will be hydrogenated are oleic acid (18:1), linoleic acid (18:2), and linolenic acid (18:3).

For a single-phase electrocatalytic hydrogenation, the reaction medium comprises the fatty acid and/or triglyceride reactant(s) and water and/or suitably chosen organic solvent(s). A suitably chosen supporting electrolyte salt is added to the reaction medium to increase the electrical conductivity of the solution. The salt and solvent can be chosen to produce a single phase liquid reaction medium (electrolyte). If necessary, sufficient organic solvent is added to solubilize the salt and reactant(s). For example, a single phase electrolyte is produced when a mixture of t-butanol, water, oil, and the hydrotropic salt tetraethylammonium p-toluenesulfonate or a mixture of t-butanol, water, oil, and sodium lauryl sulfate are combined in the correct proportions.

For a two-phase electrocatalytic hydrogenation, the reaction medium (electrolyte) comprises an oil/water dispersion (emulsion). The water phase contains a supporting electrolyte salt such as sodium sulfate or sodium lauryl sulfate. For the production of food-grade saturated or partially saturated products, the use of food-grade organic solvents and food grade supporting electrolyte salts is preferred.

Suitable organic solvents for use with edible oils or fats include $C_1$–$C_7$ alcohols such as ethanol or t-butanol. Suitable organic solvents for use with non-edible oils or fats include $C_1$–$C_7$ alcohols, dimethylformamide, and tetrahydrofuran.

Suitable salts include emulsifying salts, such as sodium lauryl sulfate; hydrotropic salts such as tetraethylammonium p-toluenesulfonate and sodium p-toluenesulfonate; quaternary ammonium salts such as tetraethylammonium chloride; inorganic salts such as sodium sulfate, potassium or sodium phosphate monobasic, and sodium chloride; and organic salts such as ammonium acetate, sodium acetate, and sodium methoxide. One or more of these salts can be mixed together. Not all of these salts ma be applicable in both single-phase and two-phase liquid mediums.

Both the supporting electrolyte salt and the organic solvent must not interfere with the electrocatalytic production of hydrogen at the catalytic cathode. Additional compounds can be present in the reaction medium provided they do not react deleteriously with the reactants and do not interfere with hydrogen generation at the cathode.

The cathode employed in this process comprises a finely divided metal powder including Raney-type metals (e.g., nickel, cobalt, copper, molybdenum), Raney alloys (e.g., nickel-molybdenum and nickel-cobalt), and high surface area precious (noble) metals (e.g., platinum black, ruthenium black, and palladium black as well as palladium-loaded carbon powder). A granular Raney catalyst with a catalytically active surface can also be used.

The cathode can have several configurations. The cathode can consist of a finely divided catalyst powder layered in a bed about 1-3 mm. thick (although thicker beds have no deleterious effects on the hydrogenation reaction). The bed is prepared by allowing the catalyst particles to gravity-settle (coat) onto a flat sheet current collector. The particles in the bed must contact one another for the applied current to pass from one particle to another. The cathode can consist of a mixture of catalyst particles and an inert binder such as polytetrafluoroethylene (PTFE) sold under the trademark Teflon ®. The mixture is rolled into a flat sheet. The cathode can consist of a powdered catalyst suspended in solution by means of agitation, in which case the particles achieve the necessary potential to reduce protons (or water) by striking a target electrode which is connected to a power supply.

A suitable catalytic cathode plate can be made from Raney nickel and PTFE. About 70 g. of a 50/50 weight % nickel/aluminum catalyst is treated (as described hereafter) to remove the aluminum. The resulting 35 g. of active catalyst are mixed with about 5.0 g. of water and then thoroughly mixed with 1.6 g. of a solution of 60% PTFE in water. The catalyst/PTFE mixture is spread on a metal mesh support to a depth of between 1 and 5 mm. and a pressure of 10 kg./$cm.^2$ is applied for about 1 minute. The resulting nickel/PTFE plate is then allowed to soak in distilled water until used in an electrocatalytic reactor.

The material used for the anode is not critical. Suitable anodes include graphite, platinum, platinum-coated titanium, or ruthenium oxide titanium oxide-coated titanium (the so-called dimensionally stable anode materials). In most cases, the anode reaction will be the oxidation of water to produce oxygen gas. In some cases the anode reaction product will result from the oxidation of the organic solvent and/or supporting electrolyte salt.

The process is preferably carried out at normal atmospheric pressures and a temperatures of about 25° to about 75° C. Elevated pressures (e.g. 10–60 psig) in the reactor can be employed. High pressures have a beneficial effect by helping to maintain a high hydrogen concentration on the cathode surface.

The electrocatalytic hydrogenation reaction can be carried out in conventional electrochemical batch or flow reactors. Representative examples of such reactors are shown in FIGS. 1, 2, and 3. However, this process is not necessarily limited to the reactor configurations shown in the drawings.

Figure 1:
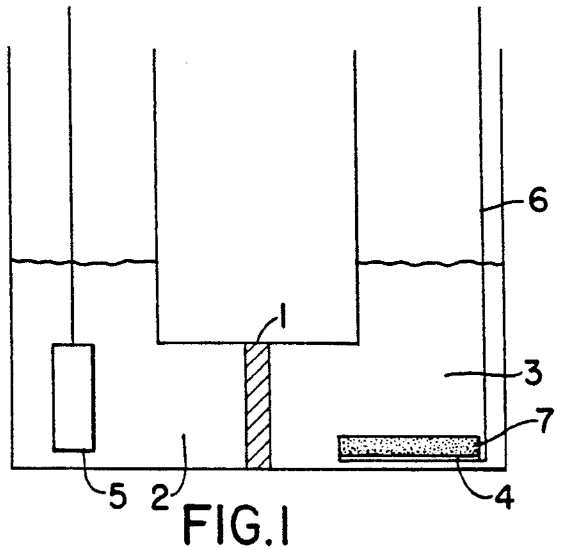
FIG. 1 is a diagram of a batch H-cell suitable for carrying out the electrocatalytic hydrogenation of an oil. A semipermeable diaphram (1) such as a glassfrit or ion exchange membrane separates the anodic compartment (2) and cathodic compartment (3). The anodic and cathodic compartments are filled with liquid electrolyte reaction medium. A flat plate nickel sheet current collector (4) is placed at the bottom of the cathodic compartment. Active catalyst powder (7) is placed on the current collector to a depth of 1–3 mm. An anode electrode (5) is placed in the anodic compartment. A nickel rod with a plastic or PTFE coating on its side wall (6) provides the electrical contact to the catalyst.
Figure 2:
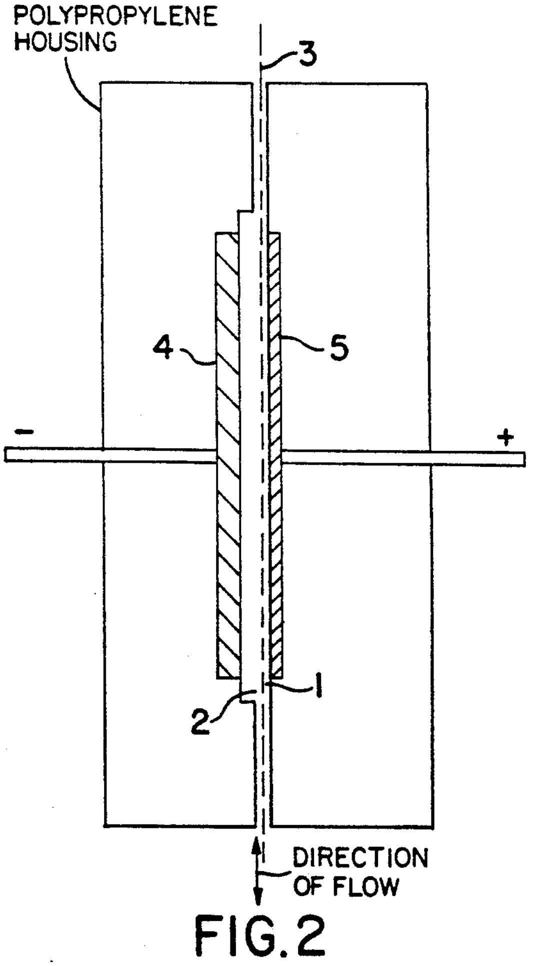
FIG. 2 is a flow reactor with perpendicular current-/electrolyte flow characteristics. The anode compartment (1) and cathode compartment (2) are separated by an ion exchange membrane (3). The cathode (4) is granular catalyst particles or a flat sheet 1–5 mm thick) of catalyst particles held together by a suitably inert binding material, such as PTFE. The anode (5) is a flat sheet, woven mesh, or expanded grid of any inert electrically conducting material. The reaction medium is pumped in either the upward or downward direction through the gap between the electrodes and the membrane separator. When the reaction medium is a two-phase oil/water dispersion, a static mixer or similar device is placed upstream of the reactor to reduce the size and increase the number of oil droplets in solution.

In the following examples, the Raney metal powder catalyst was prepared from a metal/aluminum alloy powder by adding 5.0 g. of the powder to 50.0 ml. of a 17 wt % solution of sodium hydroxide in water. Aluminum dissolution and hydrogen evolution occurred simultaneously when the powder and caustic were mixed. The solution was allowed to stand for approximately 2 hours. The sodium hydroxide solution was then removed and the active Raney metal catalyst was washed several times with distilled water until the pH of the rinse water was neutral. Raney powder catalyst prepared in this manner had an activity comparable to that of W-2.

In a typical industrial electrocatalytic hydrogenation process residual hydrogen would not have to be removed from the catalyst surface prior to its addition to the reactor. In the following examples, however, adsorbed hydrogen formed on the catalyst during the activation process was removed prior to the electrocatalytic hydrogenation experiments. This was accomplished by soaking the catalyst in oil without current flow. Removal of adsorbed hydrogen insured that the hydrogen added to the reactant was produced electrocatalytically by the applied current and was not residual adsorbed hydrogen which remained on the catalyst after the caustic soak activation. For example, 40 g. of activated Raney nickel catalyst was immersed in 100 ml. of oil. The mixture was allowed to stand with occasional stirring for about 24 hours at 50° C. After soaking, the oil/solvent solution was decanted and the catalyst was washed thoroughly with t-butanol, an aqueous 5.0 mole/l. sodium hydroxide solution, and a mixture of t-butanol and water.

EXAMPLES

Example 1

This example describes the single phase electrocatalytic hydrogenation of cottonseed oil in a batch H-cell reactor using a quaternary ammonium salt as the supporting electrolyte.

The starting solution was composed of cottonseed oil, water, salt, and t-butanol. Approximately 4.0 g. of cottonseed oil was dissolved in 150 ml. of an 11/1 volume ratio t-butanol/water solvent. The hydrotropic salt tetraethylammonium p-toluenesulfonate was added (at 0.55 mole/l.) to enhance the solubility of the oil in the medium and to serve as the supporting electrolyte. A total of 40 ml. of this solution was then added to the cathode and anode compartments of the H-cell. The H-cell was placed in a constant temperature water bath and the cathode mixture was electrocatalytically hydrogenated at atmospheric pressure (1 atm.) and a constant applied current of 22-35 milliamperes (mA). At the conclusion of the electrolysis, the t-butanol was evaporated from the reaction mixture and the oil was extracted from the salt/water solution with n-hexane.

Samples of the hydrogenated oil product dissolved in n-hexane were esterified, using standard procedures, and analyzed for changes in fatty acid composition by gas chromatography. The results are shown in Table 1.

TABLE 1

The Electrocatalytic Hydrogenation of Cottonseed Oil with Tetraethylammonium p-toluenesulfonate Salt Pressure - 1.0 atm.
Cathode - about 2.5 g. of Raney nickel (activity W-2)
Anode - graphite
Applied Current - 22-35 mA

| | | | Fatty Acid Profile (% Fatty Acid) | | | |
|---|---|---|---|---|---|---|
| Sample | Solution Temp. (°C.) | Charge Passed Coulombs | Palmitic 16:0 | Stearic 18:0 | Oleic 18:1 | Linoleic 18:2 |
| Initial Unreacted Oil | — | — | 21.8 | 2.5 | 18.1 | 54.9 |
| Hydrogenated Oil | 24 | 557 | 21.3 | 11.2 | 31.4 | 34.5 |
| Hydrogenated Oil | 57 | 713 | 21.1 | 31.6 | 26.0 | 20.2 |

The results show that the amount of stearic acid was significantly increased, that the amount of linoleic acid was significantly decreased, that the amount of oleic acid was also increased, and that the amount of palmitic acid was unchanged. The results also show that hydrogenation at the lower temperature was effective.

Example 2

This example describes the single phase electrocatalytic hydrogenation of soybean oil in a batch H-cell reactor with sodium lauryl sulfate.

Part A

Approximately 6.3 g. of soybean oil was dissolved in 150 ml. of a 10/6 volume ratio t-butanol/water solvent. Sodium lauryl sulfate was added at 1.1 mole/l. as the supporting electrolyte salt. A total of 50 ml. of the reaction mixture was then added to the compartments of the reactor and electrocatalytically hydrogenated at atmospheric pressure, a temperature of 50° C., and a constant applied current of 40 mA. At the conclusion of the electrolysis the electrolyte solution was removed from the cathodic compartment. The Raney nickel catalyst was washed with acetone to remove any oil absorbed on the catalyst surface. The acetone/oil solution was evaporated under vacuum at 60° C. to remove acetone. The remaining oil was added to the cathode compartment electrolyte. The cathode solution was then heated under vacuum at 60° C. to remove the t-butanol. The oil product was extracted from the salt water solution with n-hexane.

Samples of the hydrogenated oil product in n-hexane were esterified using standard procedures and analyzed for changes in fatty acid composition by gas chromatography.

To show that an electrocatalytic hydrogenation reaction was occurring on the Raney catalyst with the passage of current, 2.1 g. of Raney nickel catalyst were added to 50 ml. of the same reaction mixture added to the H-cell compartment. In this blank experiment, no current was passed through the catalyst. The system was heated to 50° C. and stirred occasionally for 22 hours (the same time duration as before). The oil product was then isolated, esterified, and analyzed by gas chromatography.

The results of the experiments are shown in Table 2.

TABLE 2

The Electrocatalytic Hydrogenation of Soybean Oil with Sodium Lauryl Sulfate Salt Pressure - 1.0 atm.
Cathode - about 7.0 g. Raney nickel (activity W-2)
Anode - graphite
Temperature - 50° C.

| | Fatty Acid Profile (% Fatty Acid) | | | | |
|---|---|---|---|---|---|
| Sample | Palmitic 16:0 | Stearic 18:0 | Oleic 18:1 | Linoleic 18:2 | Linolenic 18:3 |
| Initial Oil | 10.3 | 3.9 | 23.5 | 54.2 | 7.7 |
| Zero Current (blank) | 10.3 | 4.2 | 24.2 | 53.5 | 7.5 |
| 40 mA Constant Current For 3089 Coulombs | 10.5 | 27.1 | 42.3 | 18.1 | 1.30 |

The resulting hydrogenated oil has an Iodine Value of approximately 74, whereas the initial oil has an Iodine Value of 139. The partially hydrogenated product was a solid at room temperature. The resulting partially hydrogenated oil had a cis to trans oleic acid ratio of 2.9 to 1.

The results demonstrate that electric current is necessary for the reduction of the double bonds in the oil.

Part B

Similar experiments were carried out at 25° C. In this case the electrolyte consisted of a 50/50 wt % t-butanol/water mixture containing 1.0 mole/l. sodium lauryl sulfate and the same soybean oil used in Part A (2.0 g. of oil per 50 ml. of solution). A zero current blank was also carried out at 25° C. by allowing 7.0 g. of nickel catalyst to stand for approximately 20 hours in 50 ml. of t-butanol containing 2.2 g. of soybean oil. The fatty acid profile results are shown in Table 3.

TABLE 3

The Electrocatalytic Hydrogenation of Soybean Oil with Sodium Lauryl Sulfate Salt Pressure - 1.0 atm.
Cathode - about 7.0 g. of Raney nickel (activity W-2)
Anode - graphite
Temperature - 25° C.

| | Fatty Acid Profile (% Fatty Acid) | | | | |
|---|---|---|---|---|---|
| Sample | Palmitic 16:0 | Stearic 18:0 | Oleic 18:1 | Linoleic 18:2 | Linolenic 18:3 |
| Initial Oil | 10.3 | 3.9 | 23.5 | 54.2 | 7.7 |
| Zero Current (blank) | 11.0 | 4.3 | 24.5 | 52.9 | 6.8 |
| 40 mA constant current for 3000 Coulombs | 10.3 | 16.3 | 33.0 | 36.8 | 2.8 |

The resulting partially hydrogenated oil had an Iodine Value of approximately 104. It was a solid at room temperature. Based on peak areas from a gas chromatogram of the partially hydrogenated oil, the total trans isomer content of the oil product was 5.8%. The specific isomer selectivity index of the partially hydrogenated oil product was 0.166.

The results show: that (1) the electric current is necessary for the reduction of the double bonds in the soybean oil sample and (2) that the hydrogenation reaction can be carried out at near ambient temperatures.

Example No. 3

This example describes the single phase electrocatalytic hydrogenation of soybean oil in a batch H-cell reactor using a quaternary ammonium salt.

Approximately 3.0 g. of the soybean oil used in Example 2 was dissolved in 150 ml. of a 10/1 volume ratio t-butanol/water solvent. The hydrotropic quaternary ammonium salt tetraethylammonium p-toluenesulfonate was added to the solution at 1.0 mole/l. A total of 50 ml. of the mixture was electrocatalytically hydrogenated at a constant applied current of 30 mA and a temperature of 50° C. for about 12 hours. Oil was removed from the catalyst and extracted from the electrolyte solution as described in Example 2.

Esterification of the oil product and gas chromatographic analysis were performed to obtain the fatty acid profile.

The results are shown in Table 4.

TABLE 4

The Electrocatalytic Hydrogenation of Soybean Oil with Tetraethylammonium p-toluenesulfonate Salt Pressure - 1.0 atm.
Cathode - about 7.0 g. of Raney nickel (activity W-2)
Anode - graphite
Temperature - 50° C.

| | Fatty Acid Profile (% Fatty Acid) | | | | |
|---|---|---|---|---|---|
| Sample | Palmitic 16:0 | Stearic 18:0 | Oleic 18:1 | Linoleic 18:2 | Linolenic 18:3 |
| Initial Oil | 10.7 | 3.9 | 23.7 | 53.8 | 7.7 |

TABLE 4-continued

The Electrocatalytic Hydrogenation of Soybean Oil with Tetraethylammonium p-toluenesulfonate Salt Pressure - 1.0 atm.
Cathode - about 7.0 g. of Raney nickel (activity W-2)
Anode - graphite
Temperature - 50° C.

| | Fatty Acid Profile (% Fatty Acid) | | | | |
|---|---|---|---|---|---|
| Sample | Palmitic 16:0 | Stearic 18:0 | Oleic 18:1 | Linoleic 18:2 | Linolenic 18:3 |
| 30 mA constant current for 3900 Coulombs | 11.3 | 14.3 | 50.4 | 21.8 | 1.5 |

The resulting partially hydrogenated oil had an Iodine Value of approximately 89. The total percentage of trans isomers was 15.7% and the specific isomer selectivity index was 0.31. The partially hydrogenated oil was a solid at room temperature.

Example 4

This example describes the electrocatalytic hydrogenation of the soybean oil used in Example 2 in a flow reactor with a PTFE-bonded Raney nickel cathode. The reaction mixture was a single liquid phase consisting of 200 ml. of a 1.0 mole/l. sodium lauryl sulfate salt dissolved in a 1:2 volume ratio of water/t-butanol. The electrolyte contained 8.0 g. of soybean oil. The cathode consisted of about 40 g. of Raney nickel powder (activity W-2) which had been mixed with a PTFE emulsion and rolled into a flat sheet, 7.7 cm. wide, 17.5 cm. long, and approximately 3 mm. thick. Before the powder was mixed with the PTFE emulsion, hydrogen on the catalyst surface (formed during catalyst activation) was removed by immersing the catalyst in 100 ml. of pure soybean oil for 20 hours at 50° C.

Figure 3:
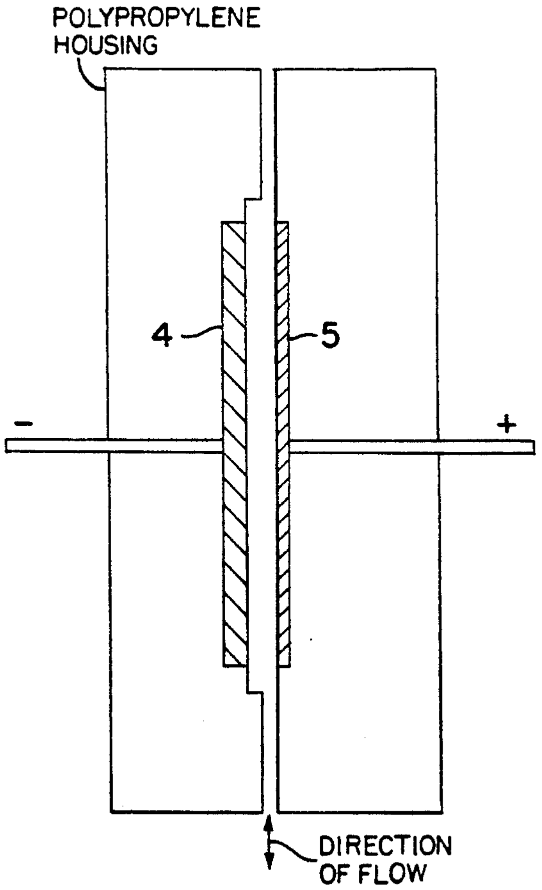
FIG. 3 is a flow reactor similar to that of FIG. 2 but without the ion exchange membrane (3) in which case there are no separate anode and cathode compartments.

An undivided flow reactor with perpendicular current/electrolyte flow characteristics (similar to that shown in FIG. 3) was used in this experiment. The reactor was placed in a batch recycle reaction loop consisting of a flowmeter, pump, and holding tank. The holding tank was immersed in a water bath to maintain constant electrolyte temperature throughout the electrolysis. The solution flow rate was set at 150 ml./min. The applied current was 301 mA. After passing 23,350 coulombs of electricity the experiment was terminated, the solution was withdrawn from the reactor, and the fatty acid profile of the reaction mixture was determined. The results of this experiment are shown in Table 5.

TABLE 5

The Electrocatalytic Hydrogenation of Soybean Oil in a Flow Reactor

Pressure - 1.0 atm.
Cathode - Teflon bonded Raney nickel plate
Anode - platinum-coated titanium
Temperature - 50° C.

| | Fatty Acid Profile (% Fatty Acid) | | | | |
|---|---|---|---|---|---|
| Sample | Palmitic 16:0 | Stearic 18:0 | Oleic 18:1 | Linoleic 18:2 | Linolenic 18:3 |
| Initial Oil | 10.7 | 3.9 | 23.7 | 53.8 | 7.7 |
| 301 mA constant current for 23,250 Coulombs | 11.0 | 24.1 | 38.8 | 24.4 | 1.5 |

The partially hydrogenated oil has an Iodine Value of approximately 83.

The results of this experiment show that the unsaturated fatty acid constituents in soybean oil can be hydrogenated electrocatalytically in a flow reactor with a single liquid phase reaction medium.

Example 5

This example describes the electrocatalytic hydrogenation of soybean oil in a flow reactor with a two-phase oil in water dispersion. The cathode consisted of PTFE-bonded Raney nickel (similar in composition and size to that used in Example No. 4). The reaction medium consisted of 200 ml. of an aqueous solution containing 0.5 mole/l. sodium phosphate monobasic and 0.5 mole/l. potassium phosphate monobasic to which 16.1 grams of the soybean oil of Example 2 was added. An undivided flow reactor with perpendicular current-/electrolyte flow, similar to that shown in FIG. 3, was used in this example. The reactor was placed in a batch recycle reaction loop consisting of a pump, holding tank immersed in a constant temperature water bath, and static mixer (placed immediately upstream of the electrocatalytic reaction to generate the oil in water dispersion). The dispersions flow rate was set at 800 ml./min. The applied current was 300 mA. The dispersion temperature was 52° C. The mixture of sodium and potassium phosphate supporting electrolytes buffered the dispersion at a pH of approximately 6.6. After passing 25,000 coulombs of electricity, the experiment was terminated, the dispersion was withdrawn from the reactor, and the fatty acid profile of the hydrogenated oil was determined by esterification and gas chromatographic analysis. The results of this experiment are shown in Table 6.

TABLE 6

The Electrocatalytic Hydrogenation of Soybean Oil in a Flow Reactor

Pressure - 1.0 atm.
Cathode - PTFE bonded Raney nickel plate
Anode - ruthenium oxide-titanium oxide coated titanium (dimensionally stable anode)
Temperature - 52° C.

| | Fatty Acid Profile (% Fatty Acid) | | | | |
|---|---|---|---|---|---|
| Sample | Palmitic 16:0 | Stearic 18:0 | Oleic 18:1 | Linoleic 18:2 | Linolenic 18:3 |
| Initial Oil | 10.7 | 3.9 | 23.7 | 53.8 | 7.7 |
| 300 mA constant current for 25,000 Coulombs | 10.9 | 14.9 | 33.8 | 36.6 | 3.4 |

The partially hydrogenated oil has an Iodine Value of approximately 106.

The results of this experiment show that the unsaturated fatty acid constituents in soybean oil can be hydrogenated electrocatalytically in a flow reactor with a reaction medium consisting of a two-phase oil in water dispersion.

Example No. 6 (Comparative)

This example describes the electrocatalytic hydrogenation of soybean oil using a flat sheet nickel plate as the cathode material. This electrode is a low hydrogen overvoltage metal but it is not a high surface area material. This is the type of catalyst used in the article discussing the hydrogenation of rubber seed oil (see the Background Of The Invention). The solution in the cathode compartment of the H-cell consisted of 60 ml. of a water/t-butanol solvent (1:2 water/t-butanol volume ratio) containing 2.05 g. of soybean oil and sodium lauryl sulfate (at a concentration of 1.0 mole/l.). The electrolyte temperature was maintained constant at 50° C. A constant current of 40 mA was applied for a sufficient time to pass a total of 3100 coulombs. At the conclusion of the electrolysis the oil was extracted from the electrolytic solution, esterified using standard procedures, and analyzed by gas chromatography. Table 5 shows the initial and final fatty acid profiles.

TABLE 7

The Electrocatalytic Hydrogenation of Soybean Oil Using a Flat Sheet Nickel Cathode Pressure - 1.0 atm.
Cathode - flat sheet nickel
Anode - graphite
Temperature - 50° C.

| | Fatty Acid Profile (% Fatty Acid) | | | | |
|---|---|---|---|---|---|
| Sample | Palmitic 16:0 | Stearic 18:0 | Oleic 18:1 | Linoleic 18:2 | Linolenic 18:3 |
| Initial Oil | 10.7 | 3.9 | 23.7 | 53.8 | 7.7 |
| 40 mA constant current for 3100 Coulombs | 10.4 | 4.5 | 24.9 | 52.2 | 7.4 |

The small variations in the initial and final fatty acid compositions are insignificant and due to gas chromatography errors. The results show that a high surface area catalyst is required for the electrocatalytic hydrogenation of the fatty acid double bonds.

Other oils such as corn oil, safflower oil, peanut oil, coconut oil, palm oil, sunflower oil and the like, which contain the same unsaturated fatty acid constituents as soybean or cottonseed oil, can be hydrogenated electrocatalytically using the procedures described in the above examples.

The invention has been described with reference to the preferred embodiments. From this description, a person of ordinary skill in the art may appreciate changes that could be made in the invention which do not depart from the scope and spirit of the invention as described above and claimed hereafter.

What is claimed:

1. A two phase electrocatalytic process for hydrogenating an unsaturated fatty acid, a triglyceride or mixtures thereof as an oil and/or a fat, which comprises the steps of:
(a) placing a dispersion consisting essentially of (i) the unsaturated fatty acid, the triglyceride, or the mixtures thereof as the oil and/or the fat, (ii) water, or a water-alcohol mixture and (iii) a supporting electrolyte salt in a reactor containing an anode and a high surface area, low hydrogen overvoltage catalytic cathode consisting essentially of a granular or a powdered Raney metal or an alloy thereof;
(b) passing current through the catalytic cathode; and
(c) generating atomic hydrogen on the catalytic cathode surface in amounts sufficient to hydrogenate some or all of the double bonds in the unsaturated fatty acid and/or triglyceride.

2. The process of claim 1, wherein the oil is a non-edible oil or fat.

3. The process of claim 2, where the oil is linseed or jojoba oil.

4. The process of claim 1, wherein the oil is an edible oil or an edible fat.

5. The process of claim 4, wherein the edible oil is an oil derived from a vegetable, a grain, a nut, or a fish and the edible fat is an animal fat.

6. The process of claim 5, wherein the oil is selected from the group consisting of safflower oil, soybean oil, sunflower oil, cottonseed oil, corn oil, canola oil, coconut oil, rice oil, peanut oil, palm oil, and olive oil.

7. The process of claim 1, wherein the catalytic cathode is a finely divided carbon powder containing a precious metal.

8. The process of claim 7, wherein the precious metal is platinum, palladium, or ruthenium.

9. The process of claim 1, wherein the catalytic cathode is the granular Raney metal or an alloy of a Raney metal.

10. The process of claim 1, wherein the catalytic cathode is a powdered Raney metal bound together in a flat sheet by use of an inert binding agent.

11. The process of claim 10, wherein the binding agent is polytetrafluoroethylene.

12. The process of claim 1, wherein the process is carried out in a batch reactor.

13. The process of claim 1, wherein the process is carried out in a continuous flow reactor.

14. The process of claim 1, wherein the supporting electrolyte salt is an organic salt, or an inorganic salt.

15. The process of claim 14, wherein the electrolyte is sodium p-toluenesulfonate or tetraethylammonium p-toluensulfonate.

16. The process of claim 1, wherein the oil or fat is an edible oil or fat and the supporting electrolyte salt is a food-grade emulsifier or an inorganic salt which is not reactive with the edible oil or fat and not reduced or oxidized during the hydrogenation.

17. The process of claim 16, wherein the food-grade emulsifier is sodium lauryl sulfate and the inorganic salt is sodium sulfate, sodium phosphate monobasic, potassium phosphate monobasic, or mixtures thereof.

18. The process of claim 1, wherein the alcohol in the water-alcohol mixture is a $C_1$–$C_7$ alcohol.

19. The process of claim 1, wherein the dispersion is water or a mixture of water and t-butanol or ethanol.

20. The process of claim 19, wherein the dispersion is water.

21. The process of claim 19, wherein the dispersion is a mixture of water and t-butanol.

22. The process of claim 19, wherein the dispersion is a mixture of water and ethanol.

23. The process of claim 1, wherein the hydrogenation is carried out at about 15° to about 75° C.

24. The process of claim 1, wherein the hydrogenation is carried out at about 25° to about 60° C.

25. The process of claim 1, wherein the hydrogenation is carried out at above 75° C.

26. The process of claim 1, wherein the catalytic cathode comprises a Raney nickel powder; wherein water is present in the two phase dispersion; wherein the supporting electrolyte salt is tetraethylammonium p-toluenesulfonate; and wherein the hydrogenation is carried out at above 75° C.

27. The process of claim 26, wherein the oil is linseed oil, jojoba oil, safflower oil, soybean oil, sunflower oil, cottonseed oil, corn oil, canola oil, coconut oil, rice oil, peanut oil, palm oil, or olive oil.

* * * * *